(12) United States Patent
Kimmlingen et al.

(10) Patent No.: US 12,222,410 B2
(45) Date of Patent: Feb. 11, 2025

(54) HEAD COIL ARRANGEMENT WITH AUTOMATICALLY POSITIONABLE SEND COIL UNIT

(71) Applicant: Siemens Healthcare GmbH, Erlangen (DE)

(72) Inventors: Ralph Kimmlingen, Zirndorf (DE); Martin Schroeder, Moehrendorf (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 16/950,198

(22) Filed: Nov. 17, 2020

(65) Prior Publication Data
US 2021/0156935 A1 May 27, 2021

(30) Foreign Application Priority Data
Nov. 26, 2019 (DE) ...................... 10 2019 218 285.2

(51) Int. Cl.
*G01R 33/341* (2006.01)
*A61B 5/055* (2006.01)
*G01R 33/34* (2006.01)

(52) U.S. Cl.
CPC ............ *G01R 33/341* (2013.01); *A61B 5/055* (2013.01); *G01R 33/34007* (2013.01)

(58) Field of Classification Search
CPC ..................................................... A61B 5/055
See application file for complete search history.

(56) References Cited

U.S. PATENT DOCUMENTS

| 5,361,765 | A  | * | 11/1994 | Herlihy | ............ | G01R 33/34046 |
|||||||324/318|
| 10,753,992 | B2 | * | 8/2020  | Ortiz   | .................. | G01R 33/3692 |
| 10,827,948 | B1 | * | 11/2020 | Tramm   | ................ | A61B 5/7405 |
| 2002/0011844 | A1 | * | 1/2002 | Biglieri | ............ | G01R 33/56383 |
|||||||324/309|
| 2006/0106302 | A1 | * | 5/2006 | Takamori | ............... | G01R 33/28 |
|||||||600/415|
| 2007/0164743 | A1 | * | 7/2007 | Takamori | ........... | G01R 33/3854 |
|||||||324/318|

(Continued)

FOREIGN PATENT DOCUMENTS

| CN | 101347330 A | 1/2009 |
| CN | 101887108 A | 11/2010 |

(Continued)

OTHER PUBLICATIONS

German Office Action for German Application No. 10 2019 218 285.2 Dated Aug. 17, 2020.

*Primary Examiner* — Dixomara Vargas
(74) *Attorney, Agent, or Firm* — Harness, Dickey & Pierce, P.L.C.

(57) ABSTRACT

A head coil arrangement is for a magnetic resonance tomograph. In an embodiment, the head coil arrangement includes a send coil unit and a receive coil unit. The send coil unit, in the position in which the head coil arrangement is normally used on a patient, is automatically positionable in the longitudinal direction of the patient relative to the head coil arrangement. A further embodiment relates to a magnetic resonance facility comprising the head coil arrangement and a guide element, embodied to transmit a force to a dog. The send coil unit is positionable via the force on the dog.

23 Claims, 6 Drawing Sheets

(56) References Cited

U.S. PATENT DOCUMENTS

| | | | |
|---|---|---|---|
| 2007/0182415 A1* | 8/2007 | Schuster | G01R 33/385 |
| | | | 324/318 |
| 2007/0285093 A1* | 12/2007 | Driemel | G01R 33/34084 |
| | | | 324/309 |
| 2008/0007259 A1* | 1/2008 | Driemel | G01R 33/3415 |
| | | | 600/410 |
| 2008/0015430 A1* | 1/2008 | Takamori | G01R 33/3415 |
| | | | 600/415 |
| 2008/0129293 A1* | 6/2008 | Schnell | G01R 33/341 |
| | | | 324/318 |
| 2008/0136412 A1* | 6/2008 | Kato | G01R 33/34084 |
| | | | 324/318 |
| 2008/0275332 A1* | 11/2008 | Alradady | G01R 33/34076 |
| | | | 324/318 |
| 2009/0021257 A1 | 1/2009 | Yasuhara | |
| 2009/0027053 A1* | 1/2009 | Decke | G01R 33/3415 |
| | | | 324/318 |
| 2010/0225321 A1* | 9/2010 | Kruip | G01R 33/3854 |
| | | | 324/318 |
| 2010/0289492 A1 | 11/2010 | Biber et al. | |
| 2012/0265053 A1* | 10/2012 | Rohr | A61B 5/055 |
| | | | 600/415 |
| 2013/0197352 A1 | 8/2013 | Paul | |
| 2013/0219620 A1* | 8/2013 | Eder | A61B 5/055 |
| | | | 5/601 |
| 2013/0307535 A1* | 11/2013 | Taracila | G01R 33/34084 |
| | | | 324/322 |
| 2013/0307540 A1* | 11/2013 | Taracila | G01R 33/283 |
| | | | 324/318 |
| 2014/0028317 A1* | 1/2014 | Friman | G01R 33/34092 |
| | | | 324/321 |
| 2014/0031671 A1* | 1/2014 | Friman | G01R 33/34007 |
| | | | 600/415 |
| 2015/0355296 A1 | 12/2015 | Harder | |
| 2017/0059674 A1 | 3/2017 | Koh et al. | |
| 2017/0248666 A1* | 8/2017 | Rothgang | G01R 33/3415 |
| 2018/0313919 A1* | 11/2018 | Ortiz | G01R 33/3692 |
| 2019/0072626 A1* | 3/2019 | Okamoto | G01R 33/34046 |
| 2019/0128978 A1* | 5/2019 | Zink | G01R 33/30 |
| 2020/0355765 A1* | 11/2020 | Chen | A61B 5/1113 |
| 2021/0018580 A1* | 1/2021 | Hou | G01R 33/34007 |
| 2021/0030306 A1* | 2/2021 | Leussler | G01R 33/36 |
| 2022/0113362 A1* | 4/2022 | Qin | H01F 27/06 |

FOREIGN PATENT DOCUMENTS

| | | |
|---|---|---|
| CN | 102961138 A | 3/2013 |
| CN | 103226188 A | 7/2013 |
| CN | 106473740 A | 3/2017 |
| CN | 110031784 A | 7/2019 |
| CN | 110301916 A | 10/2019 |
| DE | 102014210657 A1 | 1/2016 |
| JP | H07284486 A | 10/1995 |
| JP | 2005237692 A | 9/2005 |

* cited by examiner

HEAD COIL ARRANGEMENT WITH AUTOMATICALLY POSITIONABLE SEND COIL UNIT

PRIORITY STATEMENT

The present application hereby claims priority under 35 U.S.C. § 119 to German patent application number DE 102019218285.2 filed Nov. 26, 2019, the entire contents of which are hereby incorporated herein by reference.

FIELD

Embodiments of the invention generally relate to a head coil arrangement for a magnetic resonance facility, comprising a send coil unit and a receive coil unit, wherein the send coil unit, in the position in which the head coil arrangement is normally used on a patient, is positionable automatically in the longitudinal direction of the patient relative to the head coil arrangement.

BACKGROUND

Head coil arrangements are employed in magnetic resonance devices as radio frequency send coils and receive coils. The individual coils can be integrated into the housing of the head coil arrangement or attached to the housing. Moreover it is possible to accommodate the coils on printed circuit boards and to fasten these printed circuit boards to the housing via suitable fastening device(s), for example plug-in connectors.

If the coils are operating in a receive mode then the size of the coils in relation to the size of the measurement object plays a determining role for the resulting signal-to-noise ratio. The signal-to-noise ratio is optimal when the coils are positioned as near as possible to the surface of the measurement object, in this case the head. A large distance between the individual coils and the measurement object results in a poor signal-to-noise ratio. With head coils the entire head of the patient is therefore usually closely surrounded by coils.

In the development of new head coil arrangements with a greater number of individual coils it is necessary to position the individual coils even closer to the region of the body of interest, since as a result of the smaller coils the received signal intensity is lower and thus an inferior signal-to-noise ratio is achieved for the same distance.

Radio frequency send coils and receive coils are employed in particular in magnetic resonance facilities with ultra-high magnetic fields above 7 Tesla, which offer an optimum send efficiency for the respective region of the body. In order to exploit the advantage of the low signal-to-noise ratio of these devices, send and receive coils are not integrated into the patient tunnel as body coils, but are positioned as locally as possible in relation to the body. The patient tunnel in such devices above all represents a supporting tube to accommodate the patient.

With head coil arrangements the receive coil unit can be designed so that smaller cutouts are present in the area of the patient's nose and eyes. The patient can thus visually perceive a part of their environment and e.g. maintain eye contact with the medical personnel.

SUMMARY

The inventors have discovered that, with the send coil unit on the other hand, the possibilities of cutouts are very limited, since these have a negative effect on the field characteristics. With current send coil units the environment can therefore only be perceived by way of a mirror in the head coil arrangement. If the send coil unit is positioned in the measurement position on the head of the patient then direct eye contact with the medical personnel or with a relative is interrupted and the visual perception of the environment is greatly restricted. In the clinical environment this state of affairs can represent a major obstacle, especially for claustrophobically inclined patients or children and require a premature abortion of the examination.

At least one embodiment of the invention therefore provides a head coil arrangement that improves the possibility of visual contact between the patient and the medical personnel or their relatives.

Embodiments are directed to an inventive head coil arrangement and by a magnetic resonance facility.

The inventive head coil arrangement of at least one embodiment comprises:
  a send coil unit; and
  a receive coil unit, wherein the send coil unit, in a position in which the head coil arrangement is normally used on a patient, is automatically positionable in a longitudinal direction of the patient relative to the head coil arrangement.

The inventive magnetic resonance facility with a head coil arrangement of an embodiment comprises:
  the head coil arrangement of an embodiment; and
  a guide element, embodied to transmit a force to a dog, wherein the send coil unit of the head coil arrangement is positionable via the force on the dog.

BRIEF DESCRIPTION OF THE DRAWINGS

Further advantages and details emerge from the description given below of example embodiments in conjunction with the drawings. In the basic diagrams.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The inventive head coil arrangement of at least one embodiment comprises a send coil (e.g., a transmission coil) unit and a receive coil unit, wherein the send coil unit, in the position in which the head coil arrangement is normally used on a patient, is positionable automatically in the longitudinal direction of the patient relative to the head coil arrangement. A position of the head coil arrangement in which it is normally used in this case preferably represents a region of the patient's head. As used herein, the terms send coil and transmission coil are used interchangeably.

To carry out a magnetic resonance examination, the patient is usually moved in a prone position on a patient couch into a patient tunnel of the magnetic resonance facility. The head coil arrangement is usually attached to the patient couch in a predefined position, in order to avoid a relative movement between patient couch and head coil arrangement during an examination.

To accommodate the head, the receive coil unit and also the send coil unit can be supported movably on the head coil arrangement. It is conceivable for the receive coil unit and also the send coil unit to be positionable independently of one another relative to the head coil arrangement.

The send coil unit in this case is in particular positionable automatically. This can mean that the send coil unit is moved into the intended measurement position either actively via a drive or passively by utilizing a movement of a component of the magnetic resonance facility.

A drive in this case can comprise a transmission and/or a motor. To activate the drive a corresponding interface or a control element is preferably provided, which can be activated for example via a control command or a control logic in order to actively position the send coil unit.

One option for passive positioning is represented for example by the utilization of the movement of a patient couch, which at the beginning of a magnetic resonance examination is moved into the patient tunnel and can be moved out again after the conclusion of the examination. The automatic positioning of the send coil unit is preferably initiated as soon as the patient is moved via the patient couch into the patient tunnel.

It is more advantageous for the automatic positioning of the send coil unit to be initiated with the entry of the head into the patient tunnel. It is especially desirable for the automatic positioning of the send coil unit to only be initiated when the patient loses visual contact with the medical personnel because of being transported into the patient tunnel. The loss of visual contact can be determined for example as a function of a position of a head coil arrangement on the patient couch, a position of the patient couch in relation to the patient tunnel and also a diameter of the patient tunnel. It is also conceivable for the automatic positioning of the send coil unit only to be initiated after a patient's field of vision is entirely restricted by the patient tunnel.

The receive coil unit and the send coil unit are typically positionable independently of one another and can have the same initial and measurement positions. To this end the housing of the receive coil unit and of the send coil unit are preferably embodied to complement one another. This can mean that the housing of the receive coil unit and of the send coil unit are positioned for example overlapping, engaging in each other, able to be moved into one another and/or latching into one another. Since the receive coil unit can have cutouts for nose and eyes, the field of vision of the patient is usually only restricted slightly by the receive coil unit. The receive coil unit can therefore already be positioned before the magnetic resonance examination in its intended measurement position above the head of the patient. Since the head of the patient is already fixed by the receive coil, the send coil unit can be moved without danger and automatically into the intended measurement position.

The automated movement of the send coil unit into the intended measurement position therefore advantageously enables the time during which the patient's field of vision is restricted by the send coil unit to be reduced. Over and above this the patient can maintain visual contact with the medical personnel until such time as their visual contact is interrupted by the patient tunnel.

Further advantageous forms of embodiment are specified in the claims.

In accordance with a further form of embodiment the head coil arrangement has a linear guide, by which the send coil unit is positionable freely on a defined movement path. This means that the send coil unit can be moved along a known trajectory into a predetermined position. The movement path is preferably defined by a linear guide, which can be embodied as a linear structure of any given length, such as e.g. a bar, a spindle, a rail, a T profile, a slot or the like.

Linear structures in this case can be seen as all structures of which the extent definitively points in a specific direction. Such a structure can therefore likewise have a curved movement path. The send coil unit can have a corresponding mating element to the linear guide, such as e.g. an eye, a slide, a holder or a C profile.

The send coil unit can be moved with the corresponding mating element along the linear guide, wherein the direction of a longitudinal extent of the linear guide preferably matches a longitudinal direction of the patient. It is conceivable for the linear structure of the linear guide to be connected immovably to the head coil arrangement. It is likewise conceivable for the linear structure of the linear guide to be mounted on the send coil unit. The corresponding mating element can be connected to the head coil arrangement in this case.

The use of a linear guide enables the send coil unit to be guided with high precision along a linear trajectory. This enables gaps between the housings of the receive coil unit and the send coil unit and also the distance between the coils and the patient to be reduced in an advantageous manner.

In a further form of embodiment of the inventive head coil arrangement the send coil unit is supported pivotably on the head coil arrangement at a maximum angle in relation to the head coil arrangement, wherein the maximum angle between the send coil unit and the head coil arrangement is selected so that a head of a patient can be positioned unhindered in the head coil arrangement. The send coil arrangement can be supported pivotably on the head coil arrangement via a joint, a hinge or other suitable types of supports for example. The support can be attached to the head coil arrangement and/or the send coil unit.

Pivotably can mean in particular that an angle between head coil arrangement and send coil unit can be altered reversibly. The angle preferably relates in this case to a head coil arrangement arranged in parallel on the patient couch and to a send coil unit that is raised along a circular arc from the surface of the patient tunnel. The maximum angle between head coil arrangement and send coil unit can be selected so that a head can be positioned unhindered in the head coil arrangement. The angle can be greater than 60° for example. Preferably the angle is greater than 90°. An angle of between 135 and 180° is especially desirable.

It is likewise conceivable for the send coil unit in its initial position to have an angle of 180° in relation to the head coil arrangement. At the beginning of the examination the send coil unit can be pivoted to another angle, preferably an angle of 90° or less, before the patient is moved into the patient tunnel. The highest position of the send coil unit is thereby already exceeded as soon as the send coil unit is moved onto the patient couch in the patient tunnel and a collision between the two can be excluded.

A pivotably supported send coil arrangement provides an especially easy to handle and robust guidance of the send coil unit in relation to the head coil arrangement.

In a further form of embodiment the head coil arrangement has a drive for moving the send coil unit, which exerts a force on the send coil unit, so that the latter is pushed along a movement path. A drive in this case can have a facility that provides any given form of energy, which is converted into movement energy in the send coil unit. Inner energy, mechanical energy, electrical energy and radiation energy represent possible forms of energy. The drive is preferably connected to the head coil arrangement and also to the send coil unit.

It is likewise conceivable for the drive, as well as being connected to one or both of the components, also to be connected to the magnetic resonance tomograph, the patient couch and/or the receive coil unit. The drive can have a transmission, which for example converts a force, a torque or a movement and transmits it to the send coil unit. This enables an energy provided to be employed in a defined way to move the send coil unit. The drive is preferably made from a material that is compatible with the magnetic field and the electromagnetic excitations of the magnetic resonance tomograph.

It is likewise conceivable for incompatible components of the drive to be arranged outside the patient tunnel and to transmit a force or an energy to a converter, which converts the force or energy to the send coil unit into a movement. The drive can have an interface and/or a control element via which the drive is activated. The interface can be connected for example to a control logic, to the magnetic resonance tomograph or to a controller of the magnetic resonance tomograph.

The use of a drive to move the send coil unit advantageously enables the send coil unit to be activated as required and to be positioned in inaccessible positions within the patient tunnel.

In accordance with a related form of embodiment of the inventive head coil arrangement the drive for moving the send coil unit is a hydraulic or a pneumatic drive. A hydraulic drive preferably has a fluid or a mixture of fluids, which as a result of an inner energy, a potential energy and/or a kinetic energy, can transmit a force to the send coil unit. The force can be transmitted via corresponding operating elements, such as pistons or cylinders for example, but also by employing a hydro motor. The operating elements are usually connected to a line system, which transports the hydraulic fluid and couples it mechanically to the operating element. The operating elements can be connected directly or indirectly to the send coil unit.

A corresponding adaptation of surface and volume ratios of the operating elements and/or of the hydraulic lines enables any given forces and movements to be transmitted to the send coil unit. A pneumatic fluid on the other hand features a gas or a mixture of gases. The force transmission can be undertaken in a similar manner to the hydraulic drive with corresponding operating elements, which are suitable for pneumatic use. Preferably a drive for the hydraulic or pneumatic device(s) of operation is positioned outside the examination room of the magnetic resonance tomograph.

In this case the force can be transmitted via the line system, which is connected via an operating element to the send coil unit in the examination room. It is however likewise conceivable for the drive of the hydraulic or pneumatic device(s) of operation to be positioned in the examination room or to be connected to the magnetic resonance facility, e.g. to the patient couch or the head coil arrangement. A drive can be a pump, a compressor or any given drive element for example, which has a rotating, linear or oscillating drive principle.

Pneumatic and hydraulic operating media as well as the corresponding line systems can be selected so that a small interaction with a magnetic field and/or of an electromagnetic signal of the magnetic resonance facility is achieved. This enables a low-cost and magnetic resonance compatible drive system to be provided.

In a further possible form of embodiment the drive for movement of the send coil unit has a motor. This can be any given motor, which converts thermal, electrical or inner energy into mechanical work. In particular the motor can be an AC motor, a DC motor, a linear motor, a piezo motor and also a stepping or servo motor. It is conceivable for the motor to drive a pneumatic or a hydraulic device(s) of operation according to the above-mentioned example. The motor can however drive a mechanical transmission element, such as e.g. a belt drive or a shaft drive, or be coupled mechanically via a transmission to the send coil unit. If the motor is coupled via a mechanical transmission element to the send coil unit, it can be positioned outside the magnetic field of the magnetic resonance facility and be made from the usual materials for motors. If on the other hand the motor is positioned in the magnetic field of the magnetic resonance facility, the motor preferably has non-magnetic materials and a small proportion of electrically conducting structures. A possible example of a suitable motor, which operates without a magnetic field, is a piezo motor.

The use of a motor enables a defined force or movement to be created, which is transmitted to the send coil unit. This enables complex transmission elements for transmitting forces and movements to be largely avoided. This simplifies the system structure and advantageously increases the ability of the drive components to be integrated into the magnetic resonance facility.

In one form of embodiment, the head coil arrangement and/or the send coil unit have a mechanical damping element, which is embodied to accommodate the send coil unit at a stop position of the movement path with damping. A mechanical damping element can have for example a spring, an air cushion and/or an elastic or friction element, in order to avoid an abrupt braking of the send coil unit when an end point of a movement path is reached. The mechanical damping element can be fastened to the head coil unit or the send coil unit.

Preferably the mechanical damping element is positioned at a stop point at one end of a movement path of the send coil unit. It is also conceivable for the mechanical damping element to be composed of a number of elements that engage with one another, of which at least one element is connected to the send coil unit and at least one element is connected to the head coil arrangement. Such mechanical damping elements can have a shock absorber or a gas pressure spring for example.

Through the use of a mechanical damping element a movement of the send coil unit at an end of a movement path is advantageously braked with damping. This enables noises or shock impacts within the head coil arrangement to be avoided, which can upset and/or irritate a patient.

In a preferred form of embodiment of the inventive head coil arrangement, the send coil unit has a dog, wherein the dog is embodied, on mechanical contact with a guide element of the magnetic resonance facility, to transmit a force, wherein the send coil unit is positionable via the force transmission.

A dog can comprise any given three-dimensional body, such as e.g. a cube, a cylinder, a pyramid or a body homomorphic thereto, which stands out from the surface of the send coil unit. The dog is preferably fastened to the surface of the send coil unit housing. It is conceivable for the dog to be glued, welded, screwed and/or connected in some other way to the surface of the housing for this purpose. In this case detachable forms of a connection are also conceivable, in which the dog and the housing of the send coil unit engage in one another for example and/or are connected to one another via a latching element.

It is likewise conceivable for the dog to be supported movably on the housing of the send coil unit. The dog and/or the housing of the send coil unit can have a joint, a support or a spring for this purpose. The shape of the dog is embodied so that a force transmission with a guide element can be achieved. A guide element, like the dog, can represent any given three-dimensional body, which stands out from a surface of the magnetic resonance facility.

In a similar way to the dog, the guide element can be connected to a surface of the magnetic resonance facility. A surface of the magnetic resonance facility can comprise a surface of the patient couch, an outer or inner surface of the patient tunnel or a surface of a part of the housing of the magnetic resonance facility for example. The guide element is preferably positioned on the inner side of the patient tunnel, in order to obtain a force transmission with the dog. The guide element is in particular positioned on the inner side of the patient tunnel so that it makes contact with the dog at a defined point as soon as the latter is moved together with the send coil unit on the patient couch into the patient tunnel. This point is preferably selected so that a field of vision of a patient is already restricted by the patient tunnel when the dog makes contact with the guide element.

Since the send coil unit is supported movably on the head coil arrangement, a force transmission between dog and guide element leads to a displacement of the send coil unit in relation to the head coil arrangement and/or to the patient couch. In other words the send coil unit can be stopped by contact between the dog and the guide element while the patient couch moves further into the patient tunnel. The dog and the guide element preferably have a non-magnetic non-conducting material.

Through the force transmission between dog and guide element the send coil unit, because of the movement of the patient couch, can in an advantageous manner be shifted automatically into the measurement position. This enables further active components to be avoided and the head coil arrangement can be manufactured at lower cost.

In a further possible form of embodiment, the dog is connected to a drive and is designed to transmit a movement to the send coil unit. In this form of embodiment the dog can be connected to both the send coil unit and to a drive according to one of the forms of embodiment described above. A movement or a force of a drive can thereby be transmitted via the dog to the send coil unit and the position of the send coil unit can be changed in relation to the head coil arrangement. It is also conceivable for the dog to be designed as a part of the drive in this form of embodiment.

In this form of embodiment, a part of the drive can be positioned in an advantageous manner outside the magnetic field of the magnetic resonance facility and be connected mechanically to the dog of the send coil unit. The parts of the drive positioned outside the magnetic field can be manufactured at lower cost, since an interaction with a magnetic field is insignificant.

In a further form of embodiment, the dog is embodied to change an amount of a force on the guide element in the direction of movement of the send coil unit as a function of a position of the send coil unit. It is conceivable for the dog to be manufactured from an elastic material, such as e.g. an elastomer consisting of natural or silicon rubber, but also from a plastic, such as e.g. a polyethene or polyvinylchloride and to deform during force transmission with the guide element. In this case, although the dog can be elastically deformed by the force transmission with the guide element, it can still achieve a positioning of the send coil unit in the measurement position.

Over and above this, if a defined force is exceeded, e.g. when the send coil unit is located in a stop position or a measurement position, the dog can be deformed so that the guide element can be guided past the dog. The send coil unit in this case can latch in the measurement position for example or make a form fit with the head coil arrangement in the measurement position. An elastic dog enables the send coil unit already to be positioned in the measurement position even before the movement of the patient couch is completed. The elastic dog in this case is guided past the guide element with a reversible, elastic deformation.

A change in a force transmission between dog and guide element can also be understood as a dog having a geometrical shape, which opposes the guide element when they are guided against one another in a continuing direction of movement with a variable resistance. This can be achieved for example by a wedge-shaped or triangular-shaped cross section of the dog, which points with its tip in the direction of the guide element and opposes this on a side surface with a defined angle on a linear movement trajectory. When the guide element is guided along an angled side surface of the dog, as well as a force component directed in the direction of movement of the send coil unit, at least one further force component can occur, which is directed onto the angled side surface of the dog. This force directed onto the angled side surface of the dog can displace the dog e.g. from a guide or a support, so that this is removed from the movement trajectory of the guide element and dog and guide element can pass one another in this direction of movement. The dog can be supported here with a spring, a flap mechanism or an elastic or movable element for example, which opposes the guide element with a defined resistance. This resistance is preferably dimensioned so that the send coil unit, when passing the guide element, is moved into the measurement position before the dog is removed from the movement trajectory of the guide element.

In this form of embodiment, guide element and dog can be moved past one another with a defined force transmission. This allows the send coil unit to be guided past a guide element in the measurement position so that the patient on the patient couch can be moved further into the patient tunnel. This can be advantageous if, as well as the head of a patient, areas further down in the patient's body, such as e.g. the shoulders or the chest region, are to be examined. The automatic positioning of the send coil unit can thereby be realized especially easily and cost-effectively.

In a related form of embodiment, the dog is embodied to change a direction of a force on the guide element as a function of a position of the send coil unit. A direction-dependent change of the force transmission between dog and guide element can be achieved, as described above, by a wedge-shaped or triangular shaped cross section of the dog for example. In a first direction of movement the guide element can be guided along the angled side surface of the dog, wherein the force transmission between dog and guide element is dependent on the position of the send coil unit. In a second direction of movement the dog can oppose the guide element with a side surface aligned in parallel to the guide element for example, so that the two cannot pass each other or can pass each other through the application of a greater force. In this case it is especially conceivable for a dog and/or a guide element to have an elastic material, which is deformed by the action of a defined force, so that the dog and the guide element can pass one another.

It is likewise conceivable for a first dog to be coupled mechanically to a second dog, so that the second dog is moved from any given position into the movement trajectory of the guide element as soon as the first dog is taken out of the movement trajectory of the guide element. The mechanical coupling of the first dog and the second dog can be made via a pin or a lever for example, which when moved releases a lock of a first articulated joint of the first dog and simultaneously moves the second dog into the desired position and in doing so locks a second articulated joint.

With an opposing direction of movement, the pin can on the other hand release a lock of the second articulated link of the second dog, while the first dog is aligned and the first articulated joint is locked. The mechanical coupling between the two dogs is preferably embodied so that the first dog, on contact with the guide element, moves the send coil arrangement with the movement into the patient tunnel into the measurement position and is subsequently reset through the action of the force of the guide element. This enables the second dog to be set up, which on contact with the guide element moves the send coil unit with a movement of the patient couch out of the patient tunnel back into its initial position.

The form of embodiment described enables the movement of the send coil unit to be automated in an advantageous way with the aid of simple, mechanical components. This avoids unwanted influences on the imaging of the magnetic resonance facility by active motor and/or drive components.

In accordance with a further form of embodiment, the send coil unit and the receive coil unit are connected to one another in a predetermined position and are positionable relative to the head coil arrangement. The connection can be designed for example as a screw connection, glued connection, form fit, latching mechanism or as any given detachable or non-detachable fastening system. Through the connection a lly used on a patient, is able to be positioned positionable coil unit is in particular avoided. In a form of embodiment described above the send coil unit is moved into the measurement position as soon as a dog on the send coil unit rests against a guide element and the movement of the patient couch is continued in the direction of the patient tunnel.

Through the connection of the send coil unit and the receive coil unit the receive coil unit is also moved into the measurement position. The send coil unit and the receive coil unit are preferably supported movably on the head coil arrangement for this. It is conceivable for a patient's head to be supported in an open frame and/or a shaped cushion, which is connected to the head coil arrangement and does not restrict the patient's field of vision. The frame can fix the patient's head in the correct position, so that the send coil unit and the receive coil unit can be moved safely and in an automated manner into the measurement position.

The connection of the send coil unit and the receive coil unit advantageously avoids a restriction of the patient's field of vision before they enter the patient tunnel. This enables the quota of prematurely aborted magnetic resonance examinations, in particular with claustrophobic patients, to be reduced.

The inventive magnetic resonance facility with a head coil arrangement of an embodiment comprises a guide element, which is embodied to transmit a force to a dog, wherein the send coil unit is positionable by way of the force on the dog. The guide element can be connected to a surface of the magnetic resonance facility. The guide element is preferably positioned on a surface of the patient couch and/or an inner surface of the patient tunnel. In a possible form of embodiment a position of a first guide element is selected so that it makes contact with a dog at a defined point, when the latter is moved with the send coil unit on the patient couch into the patient tunnel. The force transmission between the dog and the first guide element enables the send coil unit to be moved automatically into the measurement position.

A position of a second guide element on the other hand is selected so that it makes contact with a dog at a defined point when the latter is moved out of the patient tunnel together with the send coil unit on the patient couch. This enables the send coil unit to be moved automatically into the initial position. The defined contact point between the first dog and the guide element and also the second dog and the guide element are preferably selected so that a restriction of the patient's field of vision outside the patient tunnel is avoided. It is conceivable for the magnetic resonance facility to have a number of guide elements, of which one or more interact with one or more dogs while the patient couch is moving in the direction of the patient tunnel.

It is likewise conceivable for one or more guide elements to interact with one or more dogs while the patient couch is moving in an opposite direction to the patient tunnel. One or more guide elements can also be connected to one drive as well and transmit a movement to one or more dogs or directly to the send coil unit.

Through the use of guide elements the send coil unit is advantageously positionable precisely along a movement path.

In accordance with a further form of embodiment, the guide element is embodied to change a direction of a force on the dog and/or an amount of a force on the dog in the direction of movement of the send coil unit as a function of a position of the send coil unit. For this the guide element, as described above, can have an elastic material and/or a corresponding geometrical shape and/or be supported movably, sprung or elastically. In this form of embodiment the variable amount and/or the direction of a force can act on the guide element and deform it, fold it down and/or trigger a mechanism that acts on a second guide element. A guide element can be removed by force transmission with a dog in particular from a movement trajectory of a dog and/or cause a change of position of a second guide element. The dog of the send coil unit is preferably embodied in this form of embodiment as a rigid element.

In this form of embodiment of the guide element a movement of the patient couch is able to be used in an advantageous way for automatic positioning of the send coil unit. This enables costs for active motor and drive components to be avoided.

In a further form of embodiment, the inventive magnetic resonance facility comprises a patient couch, wherein the patient couch has a guide element, which is embodied to transmit a force to the dog of the send coil unit. It is conceivable for the guide element to be positioned on an immovable part of the patient couch and/or to interact via one of the options described above with a dog of the send coil unit. The guide element in this case is in particular embodied to move the send coil unit from the measurement position into the initial position when the dog moves into contact with the guide element and the patient couch is moved in a direction opposite to the patient tunnel. In the simplest case the guide element can be embodied as a nipple, a pin or a stud.

A guide element on the patient couch enables the send coil unit to be moved automatically into its initial position using the movement of the patient couch. The effort involved in implementing an automated movement of the send coil unit using constructive device(s) can advantageously be reduced in this form of embodiment.

In accordance with a further form of embodiment, the magnetic resonance facility comprises a drive, which is connected to the guide element and exerts a force on the dog of the send coil unit. The drive is preferably embodied to move the guide element along a defined movement path. Such a movement path can be produced for example by a linear guide, a swivel bearing, a spindle transmission or the like. The drive can however also be a hydraulic or a pneumatic drive, which transmits a force and/or a movement to the guide element via a corresponding operating element. It is especially conceivable for the drive for the guide element to be coupled to a drive of the patient couch in order to obtain a movement of the guide element. The guide element can however also be connected via a coupling to the drive of the patient couch or can have its own drive, which may possibly be driven by a dedicated motor according to one of the examples described above.

In this form of embodiment, the send coil unit can be positioned independently of a movement of the patient couch. This enables a period of time for the movement of the send coil unit advantageously to be adapted in an individual way to the patient.

In a further form of embodiment of the inventive magnetic resonance facility, a drive of the guide element is connected to a motor. A force and/or a movement of the motor in this case is preferably transmitted via the drive to the guide element, in order to move the send coil unit along a defined movement path. The drive can be embodied to vary a force, a direction of movement or a deflection of the guide element. In this case all variants of mechanical, pneumatic, hydraulic and electrical drives as well as combinations thereof are conceivable. The drive is preferably coupled to a motor of the patient couch, so that a movement of the motor is transmitted via the drive to the guide element. The movement of the guide element in this case can be decoupled via a coupling from the movement of the patient couch.

It is likewise conceivable for the guide element to have its own motor. The independent motor is preferably connected to the patient couch or is positioned in the vicinity of the magnetic resonance facility. A linear motor represents a possible form of embodiment, which is positioned outside the patient tunnel and transmits a translational movement via an extension to the guide element. The extension can be a non-magnetic, non-conducting plastic rod for example, which provides a drive for the guide element. As well as this, motors are also conceivable that have non-magnetic parts and can be positioned both inside and also outside the patient tunnel.

The motor can in particular have an interface with which the motor is able to be activated via a control command. The control command can be triggered by a person, such as e.g. a doctor or a patient, by entry at a console or a remote control. It is likewise conceivable for the control command for actuation of the motor to be generated directly by the magnetic resonance facility, in order to coordinate a movement of the guide element with an imaging sequence.

The use of a motor enables the send coil unit to be positioned in an advantageous way independently of the movement of the patient couch and in coordination with the patient.

Figure 1:
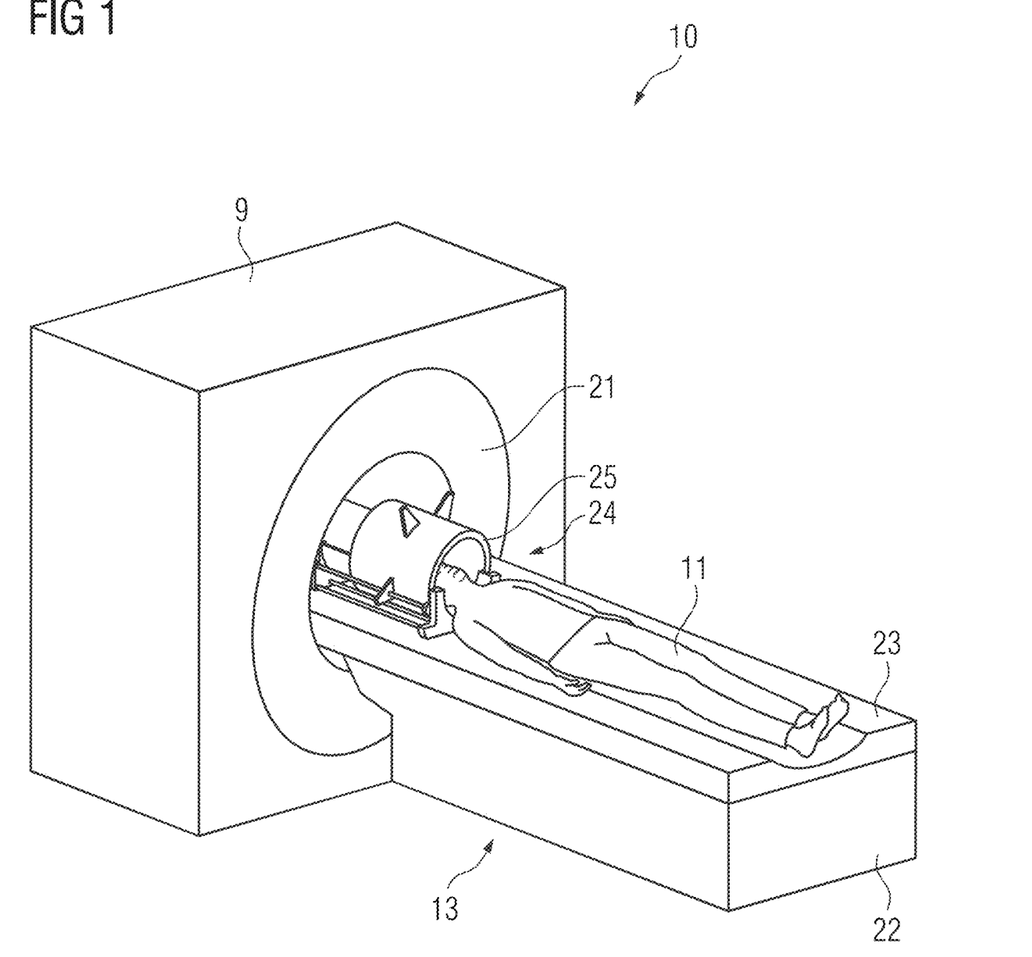
FIG. 1 shows a magnetic resonance facility with an inventive head coil arrangement of an embodiment.

Shown in FIG. 1 is a magnetic resonance facility 10, which comprises a patient couch 13 and a magnetic resonance tomograph 9. The patient couch 13 has an immovable part 22 of the patient couch 13 and a movable part 23 of the patient couch 13. The patient 11 is positioned on the movable part 23 of the patient couch 13, which can be moved to carry out a magnetic resonance examination in the patient tunnel 21 of the magnetic resonance tomograph 9.

Also located on the movable part 23 of the patient couch 13 is a head coil arrangement 24, which comprises a receive coil unit 26 (not shown) and also a send coil unit 25 and accommodates the head of the patient 11. The head coil arrangement 24 is preferably connected in a predetermined position to the movable part 23 of the patient couch 13. The movable part 23 of the patient couch 13 and the head coil unit 24 can thus be moved relative to the magnetic resonance tomograph 9 and also to the immovable part 22 of the patient couch 13. To accommodate the head of a patient 11 the send coil unit 25 and/or the receive coil unit 26 are positionable relative to the head coil arrangement 24.

Figure 2:
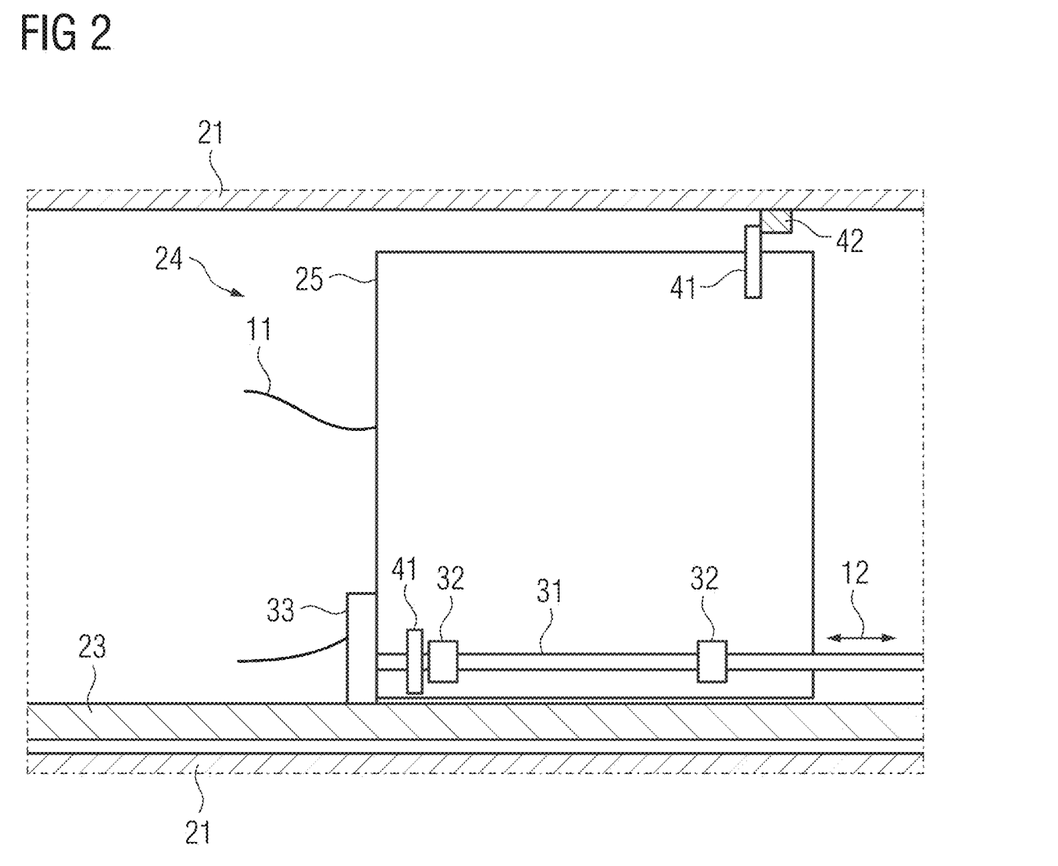
FIG. 2 shows a possible form of embodiment of an inventive head coil arrangement.

FIG. 2 shows a possible form of embodiment of an inventive head coil arrangement 24 in the patient tunnel 21 of an inventive magnetic resonance facility 10. The head of a patient 11 is supported in the head coil arrangement 24. In the example shown the patient 11 lies with their back on a movable part 23 of a patient couch 13 and is surrounded to the outside by the wall of the patient tunnel 21 of the magnetic resonance facility 10.

The send coil unit 25 surrounds the receive coil unit 26 of the head coil arrangement 24 completely and restricts the field of vision of the patient 11. The head coil arrangement 24 has a stop point 33 and also a linear guide 31. In the example shown the send coil unit 25 is supported by two holders 32 on the linear guide and can be moved on the guide in a linear way in the longitudinal direction 12 of the patient 11. The movement path of the linear guide 31 is terminated at both ends by a stop point 33, which the send coil unit 25 cannot pass. In the example shown the send coil unit 25 is located in the measurement position above the head of the patient 11. The magnetic resonance facility 10 has a guide element 42, which can make a mechanical contact with a dog 41 of the send coil unit 25.

In the present example the dog 41 is connected immovably to the send coil unit 25. If the movable part 23 of the patient couch 13 is moved out in the direction of the patient tunnel 21, then at a defined point the dog 41 makes contact with the guide element 42. The guide element 42 is preferably positioned immovably on the inner side of the patient tunnel 21 and in this way provides a resistance against the dog, which can correspond to the friction force of the send coil unit 25 on the linear guide 31. Since the send coil unit 25 is supported movably on the linear guide 31, the send coil unit 25 is shifted with a movement of the patient couch 13 in the direction of the patient 11 into the measurement position. In the form of embodiment according to FIG. 2 the measurement position simultaneously corresponds to the end position of the send coil unit 25, since this cannot be moved out beyond the stop point 33.

Figure 3:
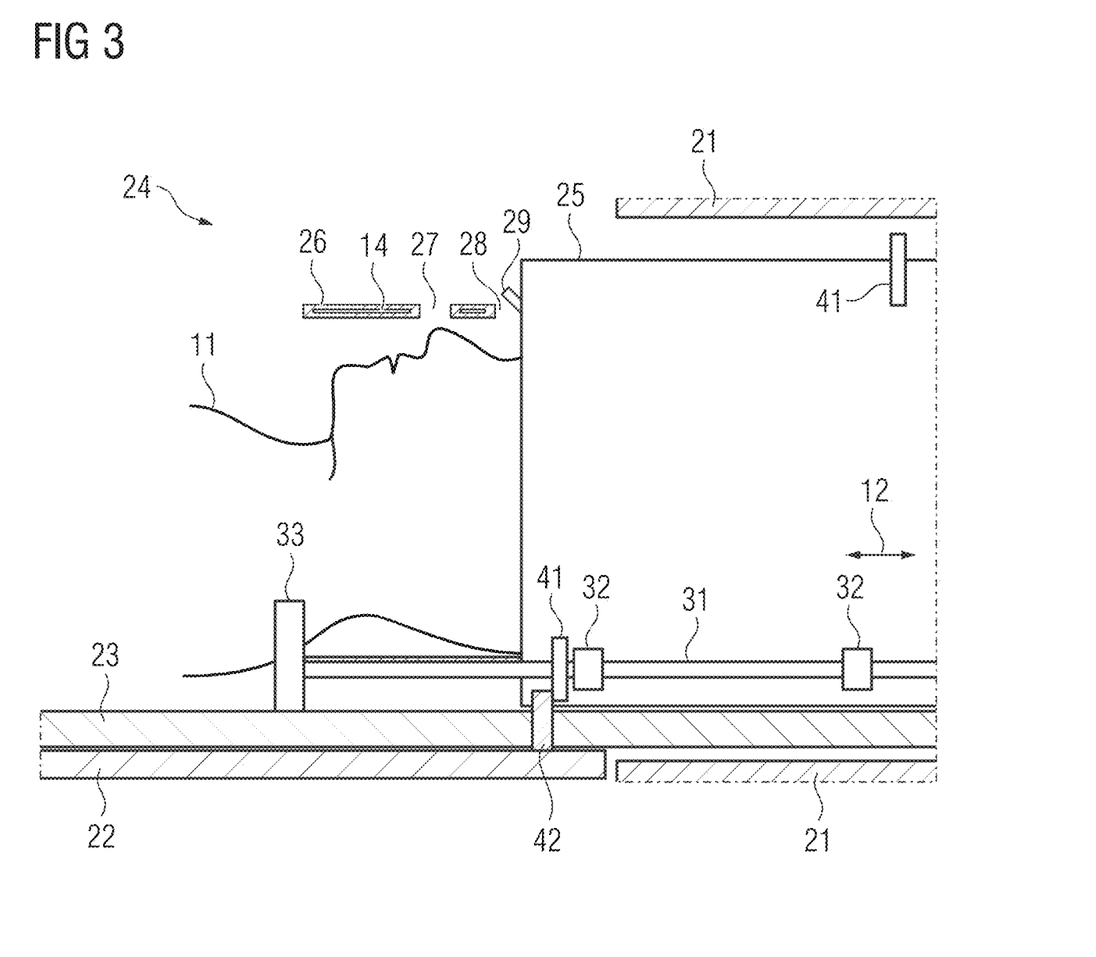
FIG. 3 shows a possible form of embodiment of an inventive head coil arrangement.

FIG. 3 shows an inventive head coil arrangement 24 when the movable part 23 of the patient couch 13 is moved out of the patient tunnel 21. A guide element 42 is positioned on an immovable part 22 of the patient couch 13 so that, at a defined point, it makes contact with a dog 41 of the send coil unit 25. Since the send coil unit 25 is supported movably on the linear guide 31, it is held by the guide element 42 in a position while the movable part 23 of the patient couch 13 with the head coil arrangement 24 is moved out of the patient tunnel 21. Since in the example shown the receive coil unit 26 is not connected to the send coil unit 25 any longer, it remains in the measurement position and is moved with the head coil arrangement 24 out of the patient tunnel 21. The receive coil unit 26 preferably has a nose cutout 27, an eye cutout 28 and also a mirror 29. The field of vision of the patient 11 is therefore only slightly restricted, so that usually there is not likely to be an abortion of the examination by the patient 11.

In this example the receive coil unit 26 is moved via a separate mechanism out of the measurement position into the initial position. It is conceivable here for the receive coil unit 26 to be able to be shifted manually within the send coil unit 25. It is likewise conceivable for the receive coil unit 26 to be supported together with the send coil unit 25 on the linear guide 31 of the head coil arrangement 24 or to have a separate linear guide. The cross section through the wall of the receive coil unit 26 in FIG. 3 shows schematically how the coils 14 can be integrated into the receive coil unit 26. A similar type of integration is also conceivable for the send coil unit 25.

Figure 4:
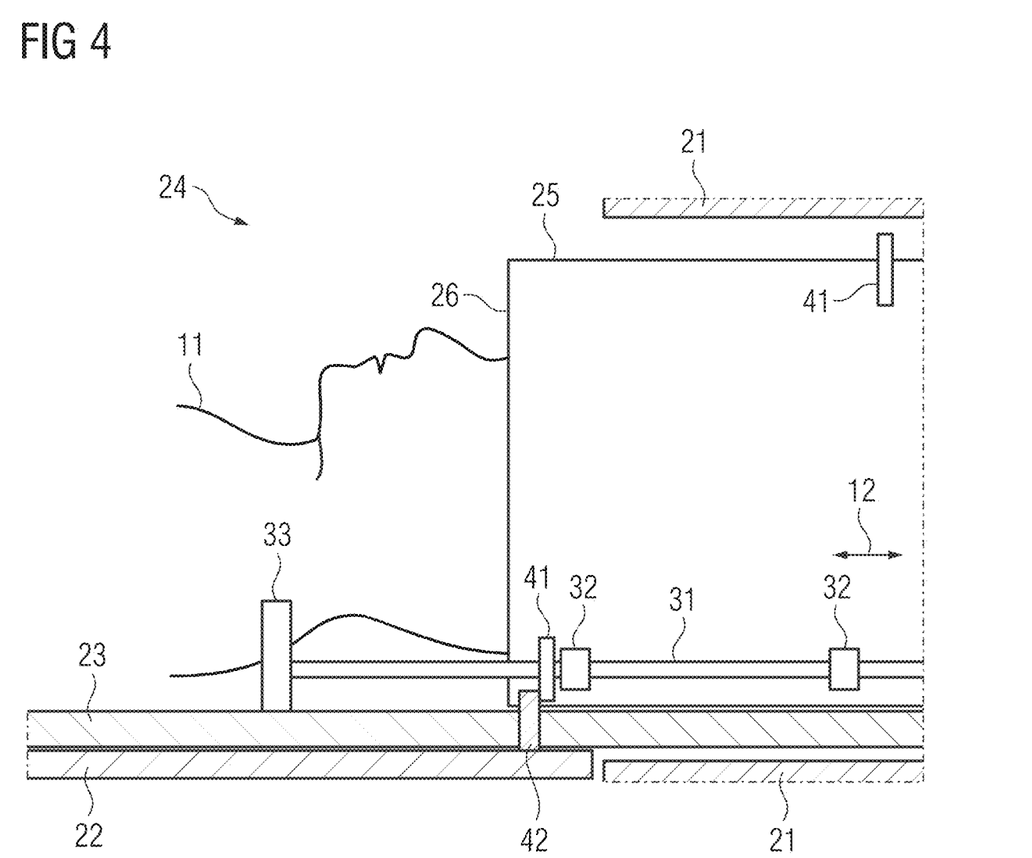
FIG. 4 shows a possible form of embodiment of an inventive head coil arrangement.

Shown in FIG. 4 is a form of embodiment of the head coil arrangement 24 in which the send coil unit 25 and the receive coil unit 26 are connected to each other in a predetermined position. Preferably the receive coil unit 26 is connected in a form fit to the send coil unit 25 and can be moved together with the send coil unit 25 on the linear guide 31 of the head coil arrangement 24. In this form of embodiment the field of vision of the patient 11 is only restricted when the movable part 23 of the patient couch 13 is moved into the patient tunnel 21. This enables the patient 11 to maintain eye contact with the medical personnel until such time as the contact is interrupted by the patient tunnel 21. The guide element 42 in the patient tunnel 21 is preferably positioned so that the assembly consisting of send coil unit 25 and receive coil unit 26 is only moved into the measurement position within the patient tunnel 21.

It is conceivable for the head coil arrangement 24 to have a fixing (not shown), such as e.g. a lateral support or a shaped neck cushion, which limits a movement of the head in the head coil arrangement 24. Through this the head of the patient can be supported in a correct position, which is preferably coordinated with the measurement position of the send coil unit 25 and the receive coil unit 26. Over and above this it can be ensured by the fixing of the head that the patient 11 is not injured by the automatic shifting of the send coil unit 25.

Figure 5:
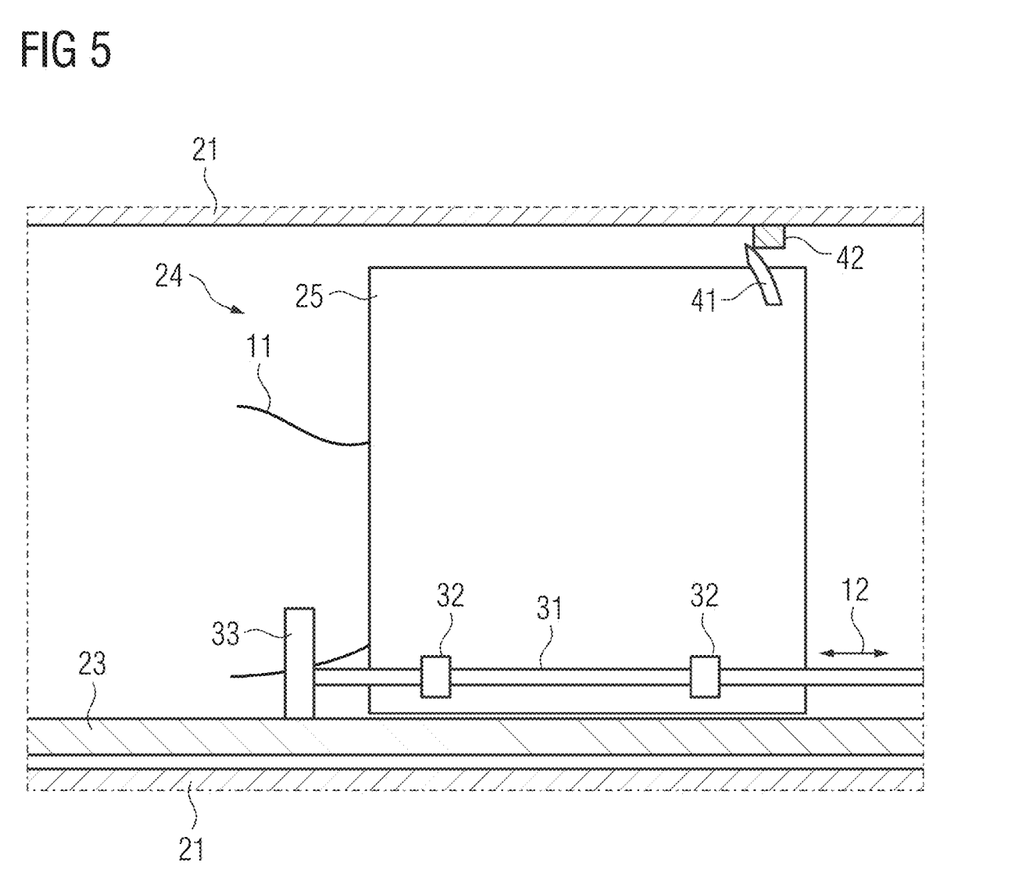
FIG. 5 shows a possible form of embodiment of an inventive head coil arrangement.

FIG. 5 shows a form of embodiment in which the dog 41 has an elastic material. The dog 41 is deformed by contact with the guide element 42 of the magnetic resonance facility 10. A force necessary to deform the elastic material is preferably greater than the friction resistance of the send coil unit 25, so that the unit is shifted into the measurement position when the movable part 23 of the patient couch 13 is moved in the direction of the patient tunnel 21. If the send coil unit 25 is resting in the example shown against the stop point 33, the force effect on the dog 41 increases as the movement of the movable part 23 of the patient couch 13 progresses. The force on the dog 41 can finally be great enough for it to deform further and slide past the guide element 42.

The send coil unit 25 is then located in the measurement position and the patient 11 can be moved further into the patient tunnel 21. With an opposing movement of the patient couch, e.g. when the patient 11 is moved out of the patient tunnel 21, the dog 41 can contact the guide element 42 mechanically from the opposite side. Through this the send coil unit 25 with the movement of the movable part 23 of the patient couch 13 is shifted automatically out of the measurement position into the initial position, which is located at a stop point 33 at the opposite end of the linear guide 31 (not shown).

Figure 6:
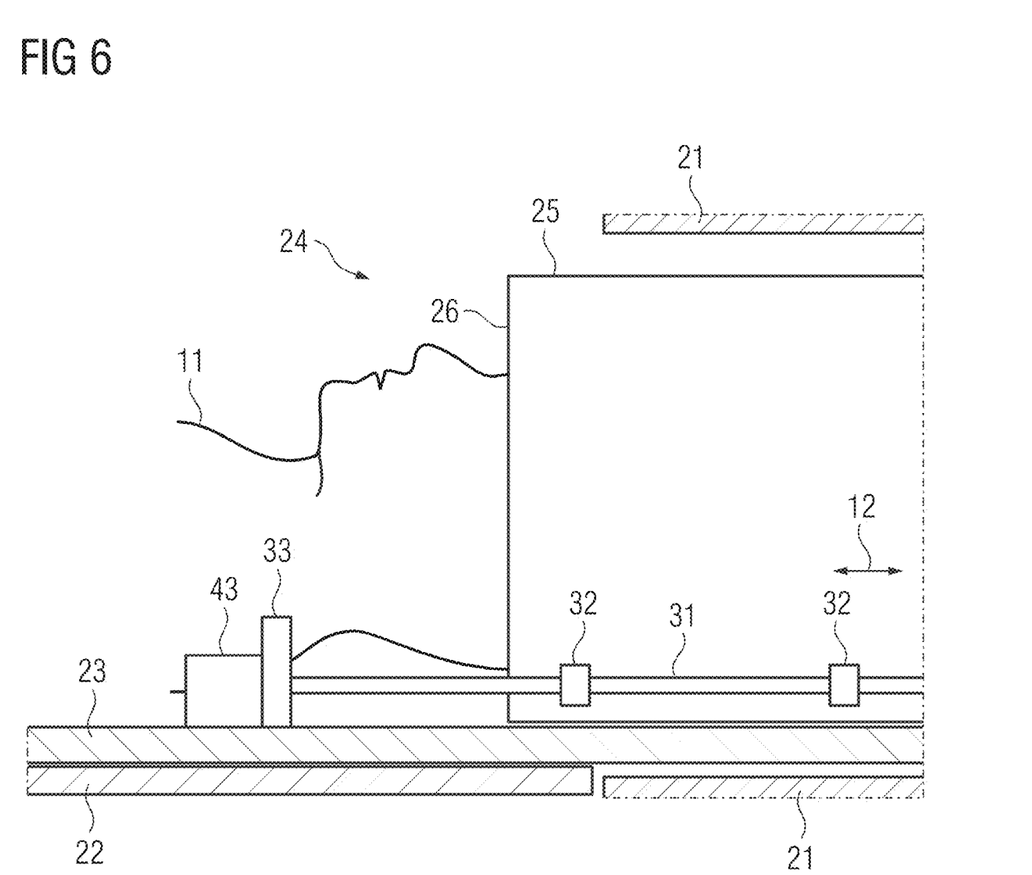
FIG. 6 shows a possible form of embodiment of an inventive head coil arrangement.

In one possible form of embodiment a motor 43 is provided, which can move the send coil unit directly or via a drive 25. In FIG. 6 a motor 43 is positioned by way of example on the immovable part 22 of the patient couch 13. The motor 43 drives a spindle 31, which at the same time is used as a linear guide 31 of the send coil unit 25. The holders 32 can have a thread for this, which engages in the thread of the spindle 31. A rotational movement of the spindle 31 leads to a transport of the send coil unit 25 by shifting the holders 32 along the spindle 31. The direction of movement of the send coil unit 25 can be set in this example via the direction of rotation of the motor 43. The spindle 31 and the holders 32 can be made of plastic for example. The motor can be positioned on the immovable part 22 of the patient couch 13 outside the magnetic field of the magnetic resonance facility 10.

In FIG. 6 the holders 32 simultaneously fulfill the function of the dog 41, with which a movement and/or a force is transmitted to the send coil unit 25. As well as the spindle 31 further drives, such as e.g. belts, toothed wheels and also hydraulic or pneumatic operating elements, are also conceivable.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A head coil arrangement for a magnetic resonance facility, the head coil arrangement comprising:
a receive coil including a first housing; and
a transmission coil including a second housing, the transmission coil configured to be
automatically positioned by being moved, in a longitudinal direction of a patient, towards the receive coil while the receive coil is stationary from the perspective of the transmission coil, and
connected to the head coil arrangement by the automatic positioning via the second housing latching into the first housing.

2. The head coil arrangement of claim 1, further comprising:
a linear guide,
wherein the transmission coil is configured to be positioned freely along the linear guide on a defined movement path.

3. The head coil arrangement of claim 1,
wherein the transmission coil is pivotably supported on the head coil arrangement at a maximum angle in relation to the head coil arrangement, and
wherein the maximum angle between the transmission coil and the head coil arrangement allows a head of the patient to be unhindered in the head coil arrangement.

4. The head coil arrangement of claim 1, further comprising:
a drive configured to move the transmission coil along a movement path by exerting a force on the transmission coil.

5. The head coil arrangement of claim 4, wherein the drive is a hydraulic drive or a pneumatic drive.

6. The head coil arrangement of claim 4, wherein the drive includes a motor.

7. The head coil arrangement of claim 2, wherein at least one of the head coil arrangement or the transmission coil includes a mechanical damping element configured to accommodate the transmission coil at a stop position with damping.

8. The head coil arrangement of claim 1,
wherein the transmission coil includes a dog configured to position the transmission coil by transmitting a force in response to mechanical contact with a guide element of the magnetic resonance facility.

9. The head coil arrangement of claim 8, wherein the dog is connected to a drive and the dog is configured to transmit a movement to the transmission coil.

10. The head coil arrangement of claim 8, wherein the dog is configured to vary an amount of the force on the guide element in a direction of movement of the transmission coil as a function of a position of the transmission coil.

11. The head coil arrangement of claim 8, wherein the dog is configured to vary a direction of the force on the guide element as a function of a position of the transmission coil.

12. The head coil arrangement of claim 1, wherein the transmission coil and the receive coil are operably connected and are configured to be positioned relative to the head coil arrangement.

13. A magnetic resonance facility comprising:
the head coil arrangement of claim 1; and
a guide element configured to transmit a force to a dog, wherein the transmission coil is configured to be positioned via the force on the dog.

14. The magnetic resonance facility of claim 13, wherein the guide element is configured to vary at least one of a direction of a force on the dog or an amount of a force on the dog in a direction of movement of the transmission coil as a function of a position of the transmission coil.

15. The magnetic resonance facility of claim 13, further comprising:
a patient couch including a guide element configured to transmit a force to the dog of the transmission coil.

16. The magnetic resonance facility of claim 13, further comprising:
a drive connected to the guide element, the drive configured to exert a force on the dog.

17. The magnetic resonance facility of claim 16, wherein the drive is connected to a motor.

18. The head coil arrangement of claim 2,
wherein the transmission coil is pivotably supported on the head coil arrangement at a maximum angle in relation to the head coil arrangement, and wherein the maximum angle between the transmission coil and the head coil arrangement allows a head of the patient to be unhindered in the head coil arrangement.

19. The head coil arrangement of claim 2, further comprising:
   a drive configured to move the transmission coil along a movement path by exerting a force on the transmission coil.

20. The head coil arrangement of claim 19, wherein the drive is a hydraulic drive or a pneumatic drive.

21. The head coil arrangement of claim 1, wherein the transmission coil is further configured to initiate the automatic positioning of the transmission coil in response to a head of the patient entering a patient tunnel of the magnetic resonance facility.

22. The head coil arrangement of claim 1, wherein the receive coil is stationary with respect to a patient couch when the transmission coil is automatically positioned.

23. The head coil arrangement of claim 1,
   wherein the receive coil is configured to be positioned above a head of the patient, and
   wherein the transmission coil is configured to be automatically positioned by being moved in the longitudinal direction towards the receive coil positioned above the head of the patient.

* * * * *